(12) United States Patent
Otawa

(10) Patent No.: US 12,290,423 B2
(45) Date of Patent: May 6, 2025

(54) SCANNING JIG AND METHOD AND SYSTEM FOR IDENTIFYING SPATIAL POSITION OF IMPLANT OR SUCHLIKE

(71) Applicant: Naruto Otawa, Fukuoka (JP)

(72) Inventor: Naruto Otawa, Fukuoka (JP)

( * ) Notice: Subject to any disclaimer, the term of this patent is extended or adjusted under 35 U.S.C. 154(b) by 98 days.

(21) Appl. No.: 16/615,149

(22) PCT Filed: May 2, 2018

(86) PCT No.: PCT/JP2018/017552
§ 371 (c)(1),
(2) Date: Nov. 20, 2019

(87) PCT Pub. No.: WO2019/211912
PCT Pub. Date: Nov. 7, 2019

(65) Prior Publication Data
US 2021/0038350 A1 Feb. 11, 2021

(51) Int. Cl.
*A61C 9/00* (2006.01)
*A61B 90/00* (2016.01)
(Continued)

(52) U.S. Cl.
CPC .......... *A61C 9/0053* (2013.01); *A61B 90/39* (2016.02); *A61C 8/005* (2013.01); *A61C 8/0089* (2013.01);
(Continued)

(58) Field of Classification Search
CPC ..... A61C 9/0053; A61C 8/005; A61C 8/0089; A61C 8/0001; A61C 19/04; A61C 19/045;
(Continued)

(56) References Cited

U.S. PATENT DOCUMENTS 2,675,615 A * 4/1954 Rosenberg ............. A61C 1/082
433/76
5,401,170 A * 3/1995 Nonomura ........... A61C 8/0001
433/68
(Continued)

FOREIGN PATENT DOCUMENTS

AT 15364 U2 * 5/2017
CA 2609890 A1 * 5/2008 ........... A61C 8/0001
(Continued)

OTHER PUBLICATIONS

Karl Bloier, "AT_15364_U2_translated" (Year: 2017).*
(Continued)

*Primary Examiner* — Heidi M Eide
*Assistant Examiner* — Holly T. To
(74) *Attorney, Agent, or Firm* — Kirschstein, Israel, Schiffmiller & Pieroni, P.C.

(57) ABSTRACT

A scanning jig is capable of acquiring spatial positional relationships between a patient's face and an abutment. The scanning jig is configured to identify the spatial position of an implant including the abutment placed in the patient's mouth, and includes a base to be connected to the implant, a scan target with a scan area scannable by a 3D scanner, and a connecting portion for connecting the base and the scan target. The connecting portion is connected at one end to the base in a predetermined direction and at the other end to the scan target in the predetermined direction, and has a predetermined length such that the scan target is positioned outside the mouth when the base is connected to the implant.

15 Claims, 13 Drawing Sheets

(51) Int. Cl.
*A61C 8/00* (2006.01)
*A61C 13/00* (2006.01)
*G06T 7/70* (2017.01)
*G06V 40/16* (2022.01)

(52) U.S. Cl.
CPC ........ *A61C 8/0095* (2013.01); *A61C 13/0004* (2013.01); *G06T 7/70* (2017.01); *G06V 40/166* (2022.01); *G06V 40/171* (2022.01); *A61B 2090/3904* (2016.02); *A61B 2090/3937* (2016.02); *A61B 2090/3991* (2016.02); *G06T 2207/30201* (2013.01); *G06T 2207/30204* (2013.01)

(58) Field of Classification Search
CPC . A61C 19/05; A61B 90/39; A61B 2090/3937; A61B 2090/3991; A61B 6/14
USPC .......................................................... 433/29
See application file for complete search history.

(56) References Cited

U.S. PATENT DOCUMENTS

| | | | | |
|---|---|---|---|---|
| 6,932,823 | B2* | 8/2005 | Grimm | A61B 17/1764 128/898 |
| 7,632,096 | B2* | 12/2009 | Gittleman | A61C 8/0001 433/173 |
| 7,753,910 | B2* | 7/2010 | Ritland | A61B 90/39 606/53 |
| D688,799 | S* | 8/2013 | Steinbrecher | D24/155 |
| 9,993,273 | B2* | 6/2018 | Moctezuma de la Barrera | A61B 34/30 |
| 10,258,434 | B1* | 4/2019 | Gittleman | A61C 8/0001 |
| 10,368,964 | B2* | 8/2019 | Robb | A61C 9/004 |
| 11,213,371 | B2* | 1/2022 | Funk | A61K 6/90 |
| 11,229,503 | B2* | 1/2022 | Kim | A61C 1/084 |
| 2003/0204150 | A1* | 10/2003 | Brunner | A61B 5/1127 600/590 |
| 2003/0224330 | A1* | 12/2003 | Aravena | A61C 8/0069 433/173 |
| 2004/0030236 | A1* | 2/2004 | Mazzocchi | A61B 90/39 600/414 |
| 2004/0030237 | A1* | 2/2004 | Lee | A61B 34/20 600/414 |
| 2005/0136379 | A1* | 6/2005 | Niznick | A61C 8/0001 433/173 |
| 2007/0225599 | A1* | 9/2007 | Solar | A61B 34/20 600/426 |
| 2007/0281278 | A1* | 12/2007 | Jorneus | A61C 8/0069 433/173 |
| 2009/0104583 | A1* | 4/2009 | Yau | A61C 8/0001 433/213 |
| 2012/0135371 | A1* | 5/2012 | Jahn | G03B 21/132 433/72 |
| 2012/0141951 | A1* | 6/2012 | Bellanca | A61C 19/04 700/98 |
| 2013/0131504 | A1* | 5/2013 | Daon | A61B 90/39 600/426 |
| 2013/0196290 | A1* | 8/2013 | Herrington | A61C 8/0068 433/173 |
| 2013/0273492 | A1* | 10/2013 | Suttin, Sr. | A61B 1/24 433/29 |
| 2014/0205966 | A1* | 7/2014 | Sogo | A61B 6/5223 433/29 |
| 2014/0377714 | A1* | 12/2014 | Jahn | A61C 1/084 433/29 |
| 2015/0147714 | A1* | 5/2015 | Daon | A61B 5/06 600/407 |
| 2015/0359479 | A1* | 12/2015 | Crandall | A61B 6/12 433/29 |
| 2016/0015488 | A1* | 1/2016 | Miltau | A61C 9/004 433/196 |
| 2017/0151038 | A1* | 6/2017 | Fan | A61C 8/0074 |
| 2017/0367804 | A1* | 12/2017 | Cordasco | A61C 19/05 |
| 2019/0167310 | A1* | 6/2019 | Felix | A61B 17/866 |
| 2019/0231284 | A1* | 8/2019 | Vartiainen | A61B 6/032 |
| 2019/0231285 | A1* | 8/2019 | Vartiainen | A61B 6/14 |
| 2019/0290365 | A1* | 9/2019 | Gao | A61B 90/39 |
| 2020/0046477 | A1* | 2/2020 | Dekel | A61B 90/39 |
| 2022/0175466 | A1* | 6/2022 | Murray | A61B 17/7076 |

FOREIGN PATENT DOCUMENTS

| | | | | |
|---|---|---|---|---|
| CN | 107184285 A | * | 9/2017 | ........ A61B 17/1703 |
| CN | 111759504 A | * | 10/2020 | |
| JP | 2009233294 A | * | 10/2009 | |
| JP | 2010-507446 | | 3/2010 | |
| JP | 2012-115668 | | 6/2012 | |
| JP | 2012-520694 | | 9/2012 | |
| KR | 20110121684 A | * | 11/2011 | |
| KR | 20130110850 A | * | 10/2013 | |
| WO | 2008051142 | | 5/2008 | |
| WO | 2010105628 | | 9/2010 | |
| WO | WO-2016126002 A1 | * | 8/2016 | ............ A61C 19/04 |
| WO | WO-2016142562 A1 | * | 9/2016 | ........... A61C 8/0001 |
| WO | 2016202967 | | 12/2016 | |
| WO | WO-2016202967 A2 | * | 12/2016 | |
| WO | WO-2018081899 A1 | * | 5/2018 | ........ A61B 17/8605 |
| WO | WO-2018228482 A1 | * | 12/2018 | |

OTHER PUBLICATIONS

Karl Bloier, "AT_15364_U2_I_translated" (Year: 2017).*
International Search Report dated Jul. 10, 2018 in International Patent Application No. PCT/JP2018/017552.

* cited by examiner

SCANNING JIG AND METHOD AND SYSTEM FOR IDENTIFYING SPATIAL POSITION OF IMPLANT OR SUCHLIKE

TECHNICAL FIELD

The present invention relates to a scanning jig for use in dental implant treatment as well as a method and system for identifying the spatial position of an implant or suchlike using the scanning jig.

BACKGROUND ART

An example of a treatment method for tooth loss is dental implant treatment. A dental implant for use in dental implant treatment includes an implant body (artificial tooth root) to be placed in a jaw bone, a prosthesis (artificial tooth), which substitutes a missing tooth, and an abutment, which connects the implant body and the prosthesis. Another example of the treatment method is an implant bridge. The implant bridge is different from the dental implant in which one implant body supports one artificial tooth. In the implant bridge, a fewer number of implant bodies support several artificial teeth connected to each other. In relation to the implant bridge, there is a treatment method called All-on-4 in which ten to 12 artificial teeth are supported by four implant bodies, and the method is used as a treatment method for the case where all teeth are missing in one or both jaws.

In producing a prosthesis for use in such dental implant treatment, an approach to producing a prosthesis using a CAD/CAM system is preferred to manual production, considering the number of man-hours and processing accuracy. With the CAD/CAM system, a prosthesis is produced based on three-dimensional intraoral impression data, and three-dimensional impression data for an implant body placed in the mouth or an implant with an abutment connected to the implant body. By referring to a simulation image generated based on the three-dimensional data, the patient can confirm the state of the prosthesis connected to the implant before prosthesis production.

Examples of the method for taking an intraoral impression and an implant impression as three-dimensional data include a method of scanning intraoral, in a state in which a dental implant scan body (See Patent Document 1) is connected to the implant, and also a method in which an intraoral impression is taken using an impression material and an impression coping, an intraoral model is produced based on the impression, and the model is scanned by a 3D scanner in a state in which the dental implant scan body is connected to the model.

However, even a prosthesis produced by a CAD/CAM system has problems in that, when the prosthesis is connected to an implant, the prosthesis's occlusal plane is not parallel to the patient's interpupillary line, or the center position of the prosthesis's front teeth deviates from the patient's facial median line. Such problems are caused because the three-dimensional data is acquired based solely on intraoral information about the patient and includes no spatial positional relationships between the implant and the patient's interpupillary line and other features.

Patent Document 2 discloses a dental impression tray for impression taking, which includes a tray portion and a handle connected to the tray. The handle has a linear portion having a length of 30 mm or more at a distal end from the tray portion. The impression creator can appropriately place the tray portion in the patient's mouth by aligning the linear portion with the patient's interpupillary line. As a result, by the impression taking that uses the dental impression tray, it is rendered possible to acquire the inclination of the occlusal plane with respect to the patient's interpupillary line. However, the dental impression tray does not take account of implant treatment, and therefore, even if the dental impression tray is used, it is not possible to acquire the spatial position of an implant body and/or other elements with respect to the face.

Furthermore, there is another problem in that with the simulation image before prosthesis production, the patient can only confirm the shape of the prosthesis and cannot confirm in advance the position of the prosthesis with respect to facial features such as the midline, the interpupillary line, and the E-line.

Patent Document 3 discloses a system and method for CAD prosthesis designing. In the system and method, a 3D scanner and CAD software are used to acquire three-dimensional data for the patient's teeth before restoration, an optical means is used to acquire data for at least a portion of the patient's face, and the patient's facial data is aligned with data for the patient's teeth before restoration and after virtual restoration, so that the patient can see a dental restoration CAD model with the aligned data. However, such data includes no spatial positional relationships between facial features and implant elements such as an implant body, and therefore, the spatial position of a prosthesis with respect to the interpupillary line and other features cannot be confirmed based on an accurate simulation image.

PRIOR ART DOCUMENTS

Patent Documents

Patent Document 1: Japanese Laid-Open Patent Publication No. 2012-115668

Patent Document 2: Japanese Translation of PCT International Application Publication No. JP-T-2010-507446

Patent Document 3: Japanese Translation of PCT International Application Publication No. JP-T-2012-520694

DISCLOSURE OF THE INVENTION

Problems to be Solved by the Invention

Therefore, a problem to be solved by the present invention is to provide a scanning jig capable of acquiring a spatial positional relationship between a patient's face and an implant body or an abutment connected to the implant body.

Solution to the Problems

To solve the problem, an embodiment of the present invention provides a scanning jig for identifying a spatial position of an implant. The implant includes an implant body placed in a patient's mouth or an abutment connected to the implant body. The jig includes a base connectable to the implant, a scan target having a scan area scannable by a 3D scanner, and a connecting portion connecting the base and the scan target. The connecting portion has a predetermined length such that, when the base is connected to the implant, the scan target is positioned outside the mouth. And at least a portion of the patient's face and the scan area are scanned by the 3D scanner with the base connected to the implant and with the scan target positioned outside the mouth, thereby acquiring three-dimensional data. And acquired three-dimensional data is analyzed, thus identifying spatial positional relationships between the portion of the face and the implant.

In a preferred embodiment of the scanning jig, the base has a predetermined height and is connected at one end to the implant and at the other end to the connecting portion.

In another preferred embodiment of the scanning jig, the base has a threaded hole for a screw by which to fix the base to the implant.

In a further preferred embodiment of the scanning jig, the connecting portion is removably connected to either the base or the scan target, or both.

In a further preferred embodiment of the scanning jig, the scan area has a flat surface.

In a further preferred embodiment of the scanning jig, the scan area has either a two-dimensional marker or a three-dimensional marker, or both.

To solve the problem, an embodiment of the present invention provides a method for identifying spatial positional relationships between a portion of the face and the implant. the method includes: connecting a scanning jig as mentioned above to the implant in the patient; acquiring three-dimensional data by the 3D scanner scanning at least a portion of the face and the scan area, with the scan target positioned outside the mouth; and analyzing the three-dimensional data, thereby identifying spatial positional relationships between the portion of the face and the implant.

To solve the problem, another embodiment of the present invention provides a method for identifying spatial positional relationships between an implant and features of a face, including any or all of the following: facial median line; interpupillary line; lip line; E-line; reference points for Camper plane; reference points for Frankfurt plane; chin; lips; mouth corners; and philtrum. The method includes: connecting a scanning jig as mentioned above to the implant; acquiring three-dimensional data by the 3D scanner scanning the scan area and a portion of the face that includes an area identifying the features of the face, with the scan target positioned outside the mouth; and analyzing the three-dimensional data, thereby identifying the features of the face and the spatial positional relationships between the implant and the features of the face.

To solve the problem, still another embodiment of the present invention provides a method for combining an image of an impression of the mouth and an image of the face. The method includes: connecting a scanning jig as mentioned above to the implant; acquiring first three-dimensional data for the mouth and the implant from the impression of the mouth and the impression of the implant; acquiring second three-dimensional data by the 3D scanner scanning at least a portion of the face and the scan area, with the scan target positioned outside the mouth; analyzing the second three-dimensional data, thereby identifying spatial positional relationships between the portion of the face and the implant; comparing a spatial position of the implant in the second three-dimensional data and a spatial position of the implant in the first three-dimensional data and applying the spatial positional relationships between the portion of the face and the implant to the first three-dimensional data, thereby identifying spatial positional relationships between the portion of the face and the first three-dimensional data; and combining an image of the mouth generated from the first three-dimensional data with an image of the portion of the face generated from the second three-dimensional data, based on the spatial positional relationships between the portion of the face and the first three-dimensional data.

To solve the problem, still another embodiment of the present invention provides a method for producing a dental prosthesis. The method includes: connecting a scanning jig as mentioned above to the implant; acquiring first three-dimensional data for the mouth and the implant from an impression of the mouth and an impression of the implant; acquiring second three-dimensional data by the 3D scanner scanning at least a portion of the face and the scan area, with the scan target positioned outside the mouth; analyzing the second three-dimensional data, thereby identifying spatial positional relationships between the portion of the face and the implant; comparing a spatial position of the implant in the second three-dimensional data and a spatial position of the implant in the first three-dimensional data and applying the spatial positional relationships between the portion of the face and the implant to the first three-dimensional data, thereby identifying spatial positional relationships between the portion of the face and the first three-dimensional data; and producing the prosthesis based on the first three-dimensional data and the spatial positional relationships between the portion of the face and the first three-dimensional data.

To solve the problem, still another embodiment of the present invention provides a method for producing an implant bridge prosthesis. The method includes: connecting scanning jigs as mentioned above respectively to a plurality of the implants connectable to one implant bridge, the plurality of the implants including a plurality of the implant bodies or a plurality of the abutments connected to the implant bodies; acquiring first three-dimensional data for the mouth and the implants from an impression of the mouth and an impression of the implants; acquiring second three-dimensional data by the 3D scanner scanning a portion of the face and the scan areas of a plurality of the scan targets, with the scan targets positioned outside the mouth, the portion of the face including an area identifying features of the face, including any or all of the following: facial median line; interpupillary line; lip line; E-line; reference points for Camper plane; reference points for Frankfurt plane; chin; lips; mouth corners; and philtrum; analyzing the second three-dimensional data, thereby identifying the features of the face and spatial positional relationships between the features of the face and the implants; comparing spatial positions of the implants in the second three-dimensional data and spatial positions of the implants in the first three-dimensional data and applying the spatial positional relationships between the features of the face and the implants to the first three-dimensional data, thereby identifying spatial positional relationships between the features of the face and the first three-dimensional data; and producing the prosthesis based on the first three-dimensional data and the spatial positional relationships between the features of the face and the first three-dimensional data.

To solve the problem, still another embodiment of the present invention provides a system for producing an implant bridge prosthesis. The system includes: scanning jigs as mentioned above connectable to a plurality of the implants connectable to one implant bridge, the plurality of the implants including a plurality of the implant bodies or a plurality of the abutments connectable to the implant bodies; a first 3D scanner acquiring first three-dimensional data for the mouth and the implants from an impression of the mouth and an impression of the implants; a second 3D scanner acquiring second three-dimensional data by scanning a portion of the face and the scan areas of a plurality of the scan targets, with the scan targets positioned outside the mouth, the portion of the face including an area identifying features of the face, including any or all of the following:

facial median line; interpupillary line; lip line; E-line; reference points for Camper plane; reference points for Frankfurt plane; chin; lips; mouth corners; and philtrum; an analyzing device 8 analyzing the second three-dimensional data, identifying the features of the face and spatial positional relationships between the features of the face and the implants, comparing spatial positions of the implants in the second three-dimensional data and spatial positions of the implants in the first three-dimensional data, and applying the spatial positional relationships between the features of the face and the implants to the first three-dimensional data, thereby identifying spatial positional relationships between the features of the face and the first three-dimensional data; and a producing device producing the prosthesis under control in accordance with three-dimensional data for the prosthesis, the three-dimensional data being created based on the first three-dimensional data and the spatial positional relationships between the features of the face and the first three-dimensional data.

Effect of the Invention

The present invention renders it possible to provide a scanning jig capable of acquiring a spatial positional relationship between a patient's face and an implant body or an abutment connected to the implant body.

MODE FOR CARRYING OUT THE INVENTION

First Embodiment

Hereinafter, a scanning jig according to the present invention, along with a method and system for producing a prosthesis using the scanning jig, will be described with reference to the accompanying drawings.

<Scanning Jig>

Figure 1A:
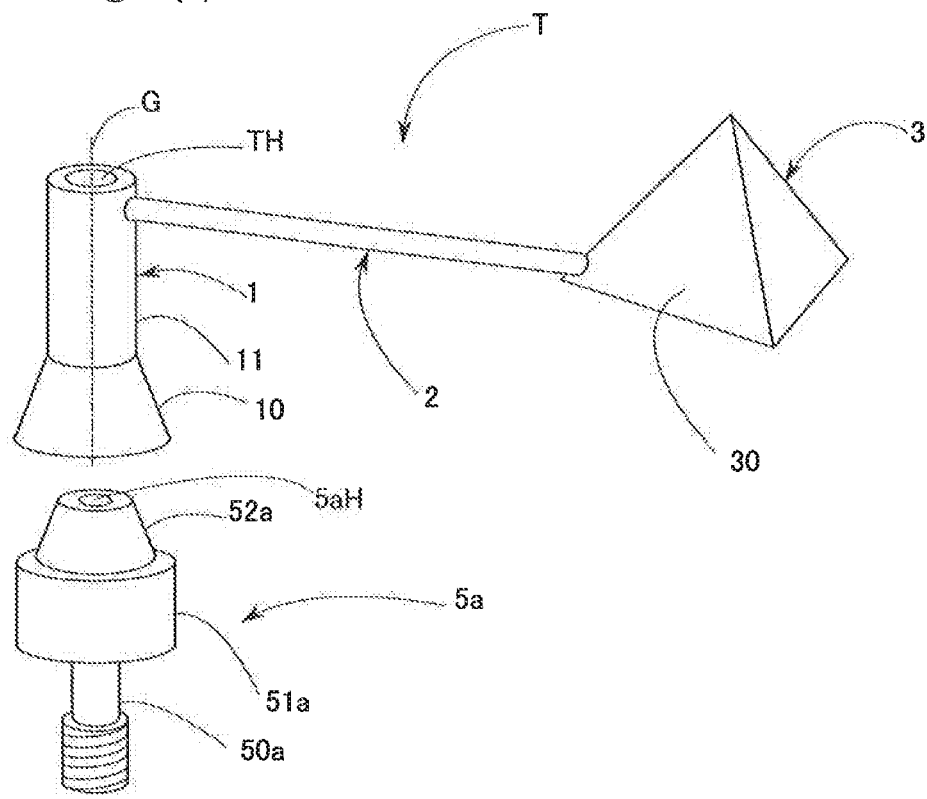
FIG. 1 provides (a) an oblique view illustrating a scanning jig of the present invention, along with an implant body and an abutment, and (b) a vertical cross-sectional view taken along the center axis of a base of the scanning jig.

FIG. 1(a) is an oblique view illustrating a scanning jig T (simply referred to below as a "jig T") according to a first embodiment of the present invention, an abutment 5a to be connected to the jig T, and an implant body 4a to be connected to the abutment 5a.

The implant body 4a and the abutment 5a are members for use in, for example, an All-on-4 implant bridge. The implant body 4a has an internally threaded round hole 4aH provided at an upper end.

The abutment 5a includes a lower connecting portion 50a, an abutment body 51a, and an upper connecting portion 52a. The lower connecting portion 50a is externally threaded. The lower connecting portion 50a is configured to be inserted into the round hole 4aH and threadedly engaged with the implant body 4a. The upper connecting portion 52a has a truncated conical shape at an upper end of which a round hole 5aH is provided along a centrally vertical axis of the upper connecting portion 52a. The round hole 5aH is internally threaded. The upper connecting portion 52a has an upper end surface provided in the form of a plane perpendicular to the centrally vertical axis of the upper connecting portion 52a.

The jig T includes a base 1, a connecting portion 2, and a scan target 3.

The base 1 has a truncated conical connecting portion 10, a base body 11 continuing from an upper end of the truncated conical connecting portion 10, and a stepped through hole TH provided at the center of an upper end surface of the base body 11.

Figure 1B:
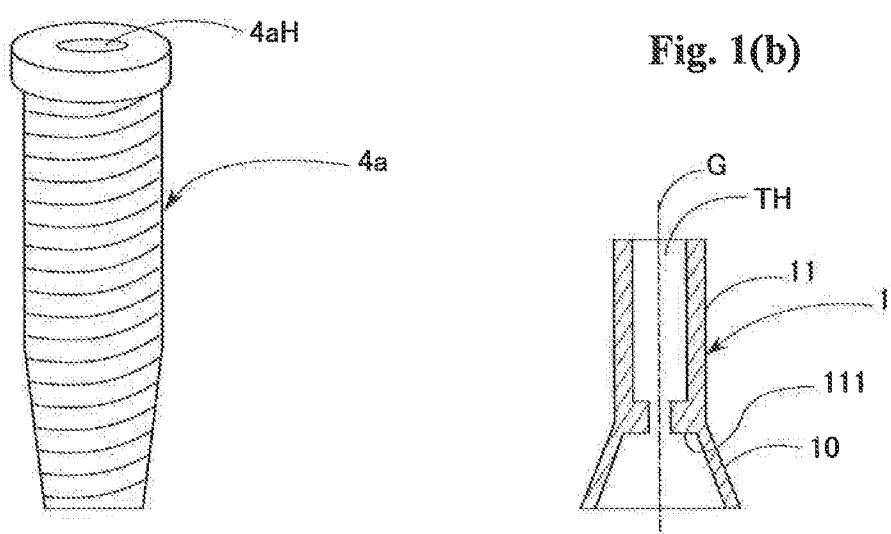

The truncated conical connecting portion 10 is configured to rotatably contact the upper connecting portion 52a of the abutment 5a. Specifically, the truncated conical connecting portion 10 has a truncated conical shape and is hollowed in the shape of a truncated cone with an inverted concave cross-section, as shown in FIG. 1(b). The truncated conical connecting portion 10 has an inner lower surface 111 to be placed in contact with the upper connecting portion 52a, and the inner lower surface 111 is formed in a plane perpendicular to the centrally vertical axis G. The external shape of the truncated conical connecting portion 10 is not specifically limited so long as the truncated conical connecting portion 10 rotatably contact the upper connecting portion 52a.

The base body 11 is formed in the shape of a cylinder extending in the direction of the centrally vertical axis G of the base 1, but this is merely an illustrative example and is not limiting.

The stepped through hole TH is provided along the centrally vertical axis G of the base 1. The stepped through hole TH is configured to receive a screw (not shown) to removably engage the base 1 with the upper connecting portion 52a.

The connecting portion 2 is connected at one end to the base 1 in a predetermined direction and at the other end to the scan target 3 in the predetermined direction. Moreover, the connecting portion 2 has a predetermined length such that, when the base 1 is connected to an abutment 5a placed in the patient, the scan target 3 is positioned outside the mouth. Preferably, the connecting portion 2 is thinner in a middle portion than the freeway space so long as the middle portion has mechanical strength that prevents deformation of the connecting portion 2. In the present embodiment, the connecting portion 2 has a bar shape, but this is merely an illustrative example and is not limiting.

The scan target 3 is a tetrahedron that can be scanned by a 3D scanner. The four faces and common edges of the tetrahedron correspond to a scan area 30 of the present invention. This definition of the scan area 30 is merely an illustrative example and is not limiting. The scan area 30 has a matte-finished white surface so as to be optimally scanned by a 3D scanner, but this is merely an illustrative example and is not limiting. Moreover, the scan target 3 is not limited to any specific shape.

The connecting portion 2 is connected to the upper end side of the base body 11. The base 1 has a predetermined height such that, when the base 1 is connected to the abutment 5a, the connecting portion 2 is prevented from contacting any intraoral portion and thereby being deformed. The predetermined height is determined based on intraoral factors such as the height of adjacent teeth.

For the jig T thus configured, for example, the shape of the jig T, along with the shape of the abutment 5a, is memorized in advance as three-dimensional data in a memory portion of an analyzing device 8 (FIG. 3), so that, when the scan area 30 is scanned by a second 3D scanner 7b (FIG. 3), the analyzing device 8 identifies the spatial position of the base 1 based on the resultant three-dimensional data D2, along with the spatial position of the abutment 5a connected to the base 1. This analysis method is merely an illustrative example and is not limiting. Moreover, the range of the scan area 30 that is to be scanned may be a portion of the area of the scan target 3 so long as it is possible to acquire the three-dimensional data D2 by which the spatial position of the base 1 can be identified.

<Method and System for Producing the Prosthesis Using the Scanning Jig of the Present Embodiment>

Next, a method and system for creating a prosthesis using the jig T will be described with reference to FIGS. 2 to 8, taking as an example All-on-4 on an edentulous lower jaw.

Figure 3:
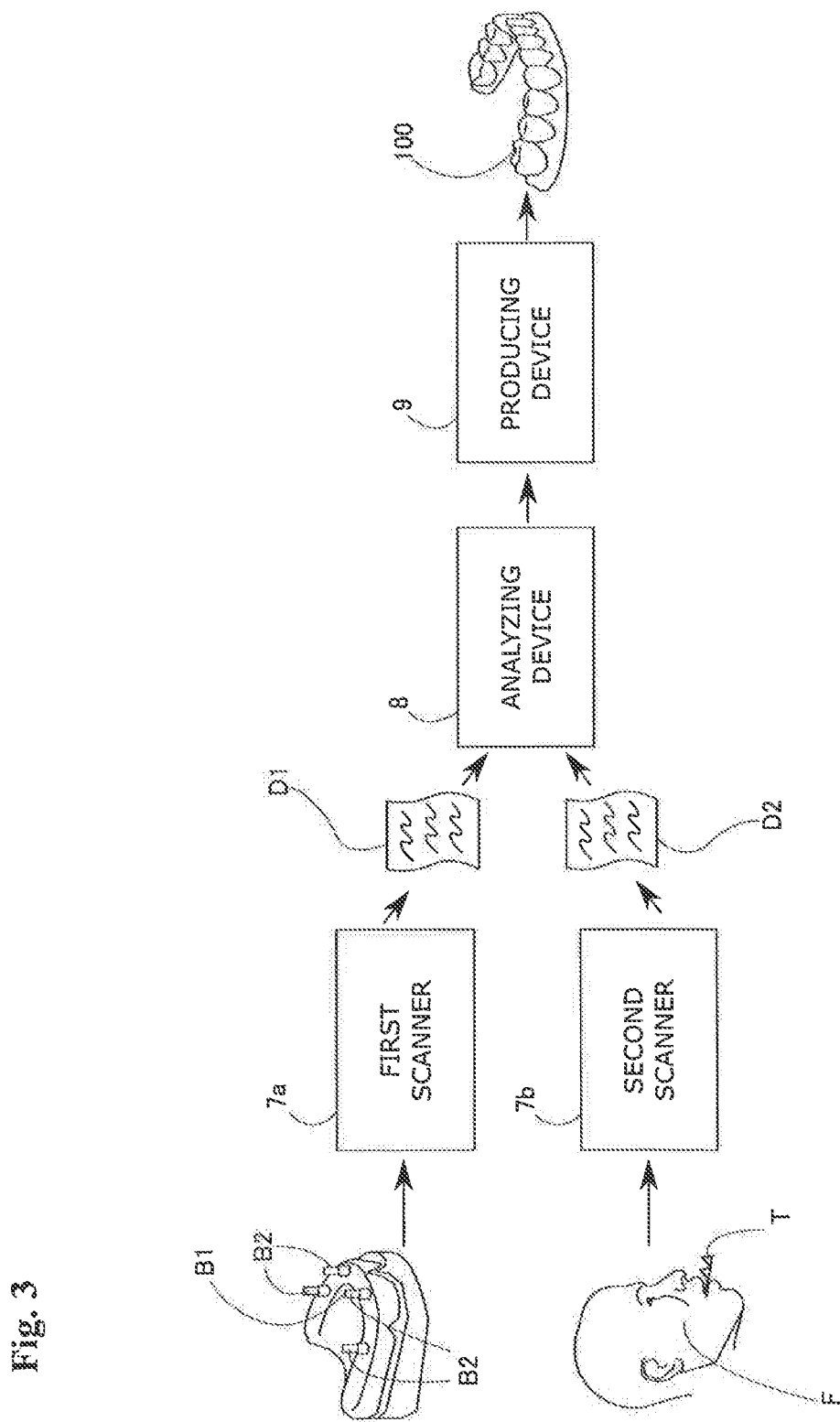
FIG. 3 is a configuration diagram of a system for producing an implant bridge prosthesis using the scanning jig in FIG. 1.

FIG. 3 is a configuration diagram of a system according to the present embodiment for producing a prosthesis 100 of an implant bridge. The system includes a jig T, a first 3D scanner 7a, a second 3D scanner 7b, an analyzing device 8, and a producing device 9. The system is configured such that (1) the first 3D scanner 7a acquires first three-dimensional data D1 by scanning an intraoral model B1 produced based on an intraoral impression and scan bodies B2 connected to the model B1, (2) the second 3D scanner 7b acquires second three-dimensional data D2 by scanning a face F and the jig T, (3) the analyzing device analyzes the first and second three-dimensional data D1 and D2, thereby identifying spatial positional relationships between features of the face F and the first three-dimensional data, and (4) the producing device 9 produces a prosthesis 100 based on the positional relationships.

In dental implant treatment, initially, a CT test is conducted before implant body placement surgery, and simulation is carried out for the implant body placement surgery on the basis of images obtained by the CT test. Then, based on the simulation, the surgery is conducted to place four implant bodies. Examples of the placement surgery include a method in which the gingiva is incised and an implant body is placed in the incision, and a method in which an implant body is placed in a hole provided by a gingiva punch without incising the gingiva. In the case where the gingiva is incised, aesthetically ideal implant treatment can be carried out by performing bone reduction based on the aforementioned simulation.

In the present embodiment, based on the simulation result, two implant bodies 4a1 and 4a2 are placed vertically to the lower jaw, and the other two implant bodies 4b1 and 4b2 are placed obliquely. The implant bodies 4a1 and 4a2, which are placed vertically to the lower jaw, are the same as the implant body 4a described above. Moreover, connected to the implant bodies 4a1 and 4a2 are abutments 5a1 and 5a2, which are the same as the abutment 5a described above.

Described next are an implant body 4b to be placed obliquely and an abutment 5b to be connected to the implant body 4b.

Figure 4:
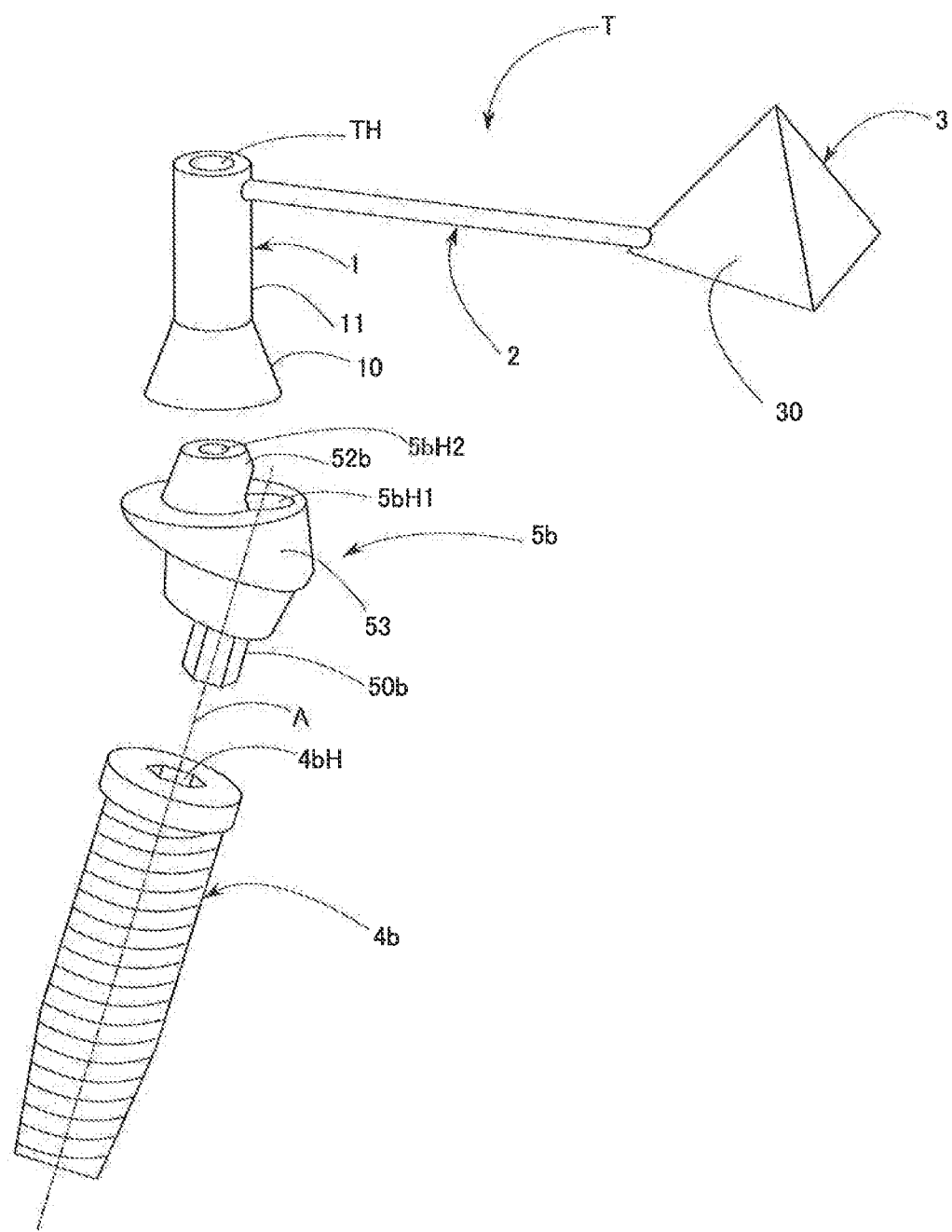
FIG. 4 is an oblique view illustrating the scanning jig in FIG. 1, along with an implant body and an abutment different from those in FIG. 1.

Referring to FIG. 4, the implant body 4b has an internally threaded hexagonal hole 4bH provided at an upper end.

Similar to the abutment 5a, the abutment 5b is a multi-unit abutment for use in All-on-4 treatment but is angle corrected. The abutment 5b has a lower connecting portion 50b, a threaded hole 5bH1, an angle-corrected portion 53, and an upper connecting portion 52b.

The lower connecting portion 50b has a hexagonal prism shape. The lower connecting portion 50b is configured to be inserted into the hexagonal hole 4bH of the implant body 4b along a centrally vertical axis A common to the implant body 4b and the lower connecting portion 50b, so as to be non-rotatably connected to the implant body 4b.

The threaded hole 5bH1 is provided so as to extend from an upper end of the angle-corrected portion 53 to a lower end of the lower connecting portion 50b along the centrally vertical axis A of the lower connecting portion 50b. The threaded hole 5bH1 is configured to receive a screw (not shown) to engage the abutment 5b with the implant body 4b.

The angle-corrected portion 53 is formed above the lower connecting portion 50b and is stepped so as to have a diameter increased in cross section. The angle-corrected portion 53 has a two-part structure consisting of upper and lower portions and bent at a transitional part from the lower to the upper portion.

The upper connecting portion 52b is disposed at the upper end of the angle-corrected portion 53. The upper connecting portion 52b has the same shape as the upper connecting portion 52a of the abutment 5a, except that a part of upper connecting portion 52b is penetrated by the threaded hole 5bH2. Accordingly, the upper connecting portion 52b is configured to be removably engaged with the base 1 by a screw (not shown) in the same manner as the upper connecting portion 52a is connected to the base 1 of the jig T.

Figure 5A:
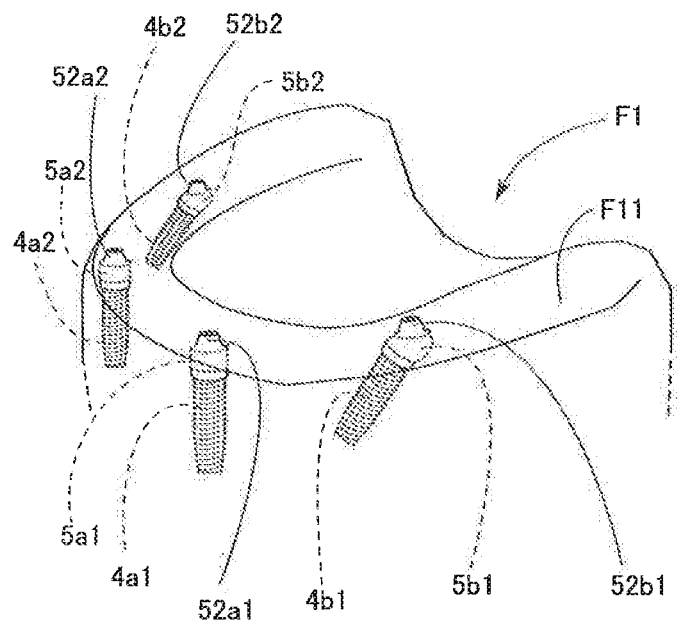
FIG. 5 provides (a) an oblique view illustrating implant bodies and abutments, as shown in FIGS. 1 and 2, placed in a lower jaw, and (b) an oblique view illustrating scanning jigs, as shown in FIG. 1, connected to the abutments.

As shown in FIG. 5(a), by implant body placement surgery, implant bodies 4a1 and 4a2 are placed upright in a front part of a patient's lower jaw F1, and implant bodies 4b1 and 4b2 are placed obliquely behind the implant bodies 4a1 and 4a2. The implant bodies 4a1, 4a2, 4b1, and 4b2 are respectively connected to abutments 5a1, 5a2, 5b1, and 5b2. Upper connecting portions 52a1, 52a2, 52b1, and 52b2 of the abutments 5a1, 5a2, 5b1, and 5b2 are exposed upward from a gingiva F11. Ideally, the placement surgery is carried out such that all of the upper connecting portions 52a1 to 52b2 are positioned as simulated on the basis of a CT test, and the upper connecting portions 52a1 to 52b2 have respective centrally vertical axes approximately parallel to one another.

Figure 2:
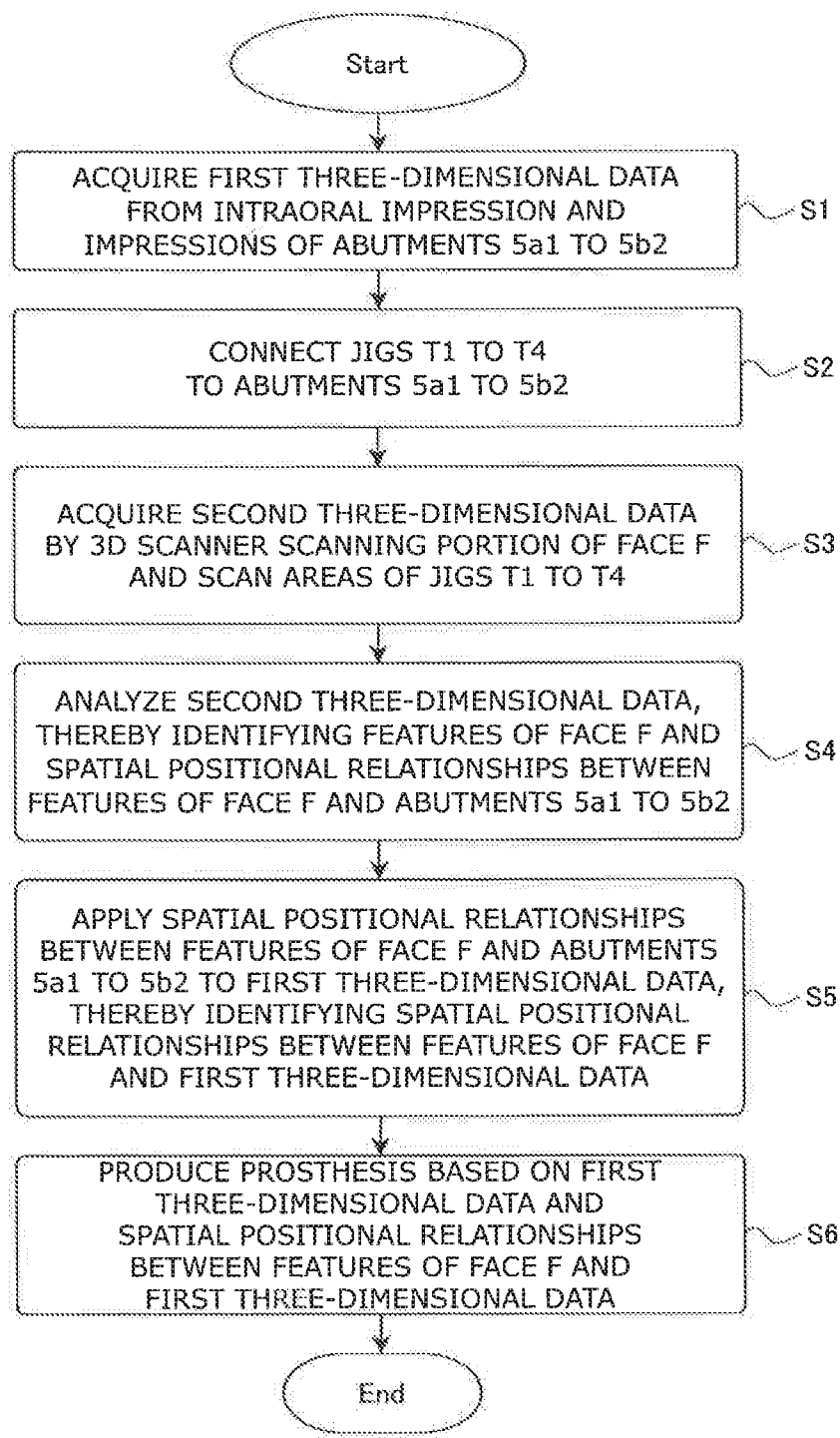
FIG. 2 is a flowchart of a method for producing a prosthesis using the scanning jig in FIG. 1.

Next, the first 3D scanner 7a acquires first three-dimensional data D1 for an intraoral impression and impressions of the placed abutments 5a1, 5a2, 5b1, and 5b2 (S1 in FIG. 2). In the present embodiment, initially, the intraoral impression is taken using an impression material and an impression coping, and based on the taken impression, an intraoral model B1 is produced, and scan bodies B2 are connected to the intraoral model B1. Thereafter, the intraoral model B1 is scanned by the first 3D scanner 7a, thereby acquiring the first three-dimensional data D1 for the intraoral impression and the impressions of the placed abutments 5a1, 5a2, 5b1, and 5b2.

Figure 5B:
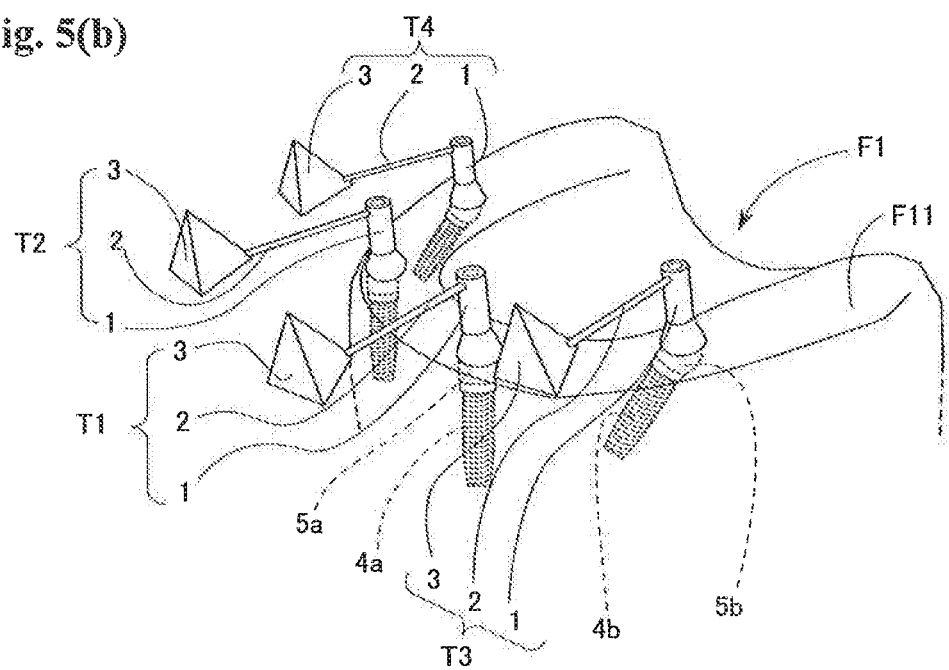

Next, as shown in FIG. 5(b), four jigs T1 to T4 are connected to and threadedly engaged with the four abutments 5a1 to 5b2, respectively, such that scan targets 3 are positioned in front (S2 in FIG. 2).

Figure 6A:
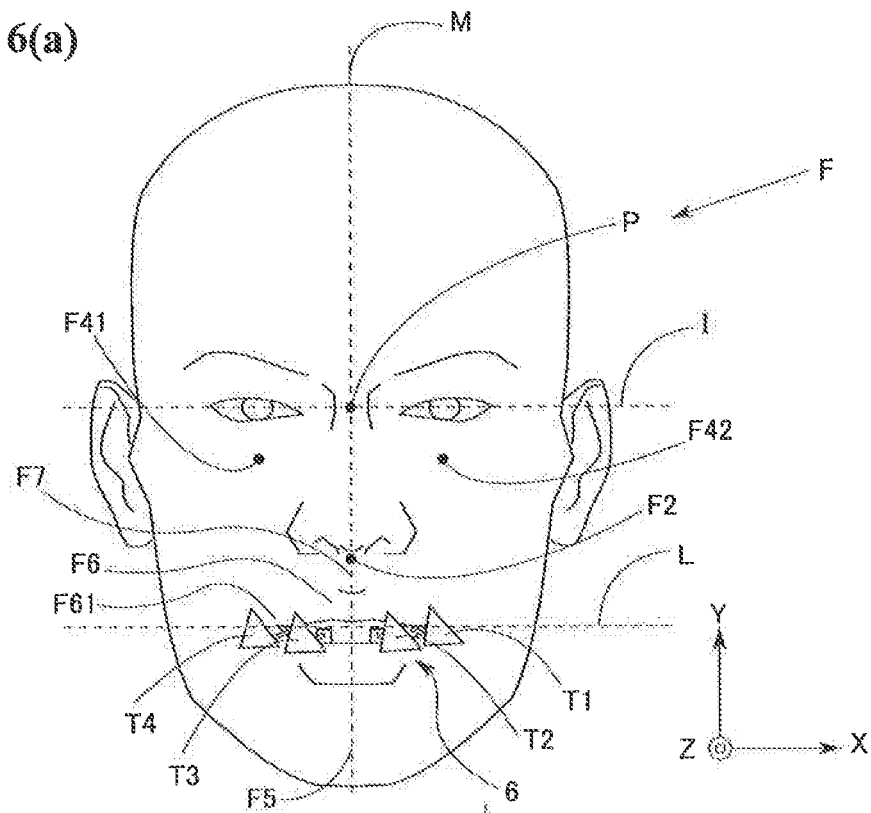
FIG. 6 provides (a) a front view and (b) a side view illustrating a face and scanning jigs, as shown in FIG. 1, connected to abutments in a mouth.
Figure 6B:
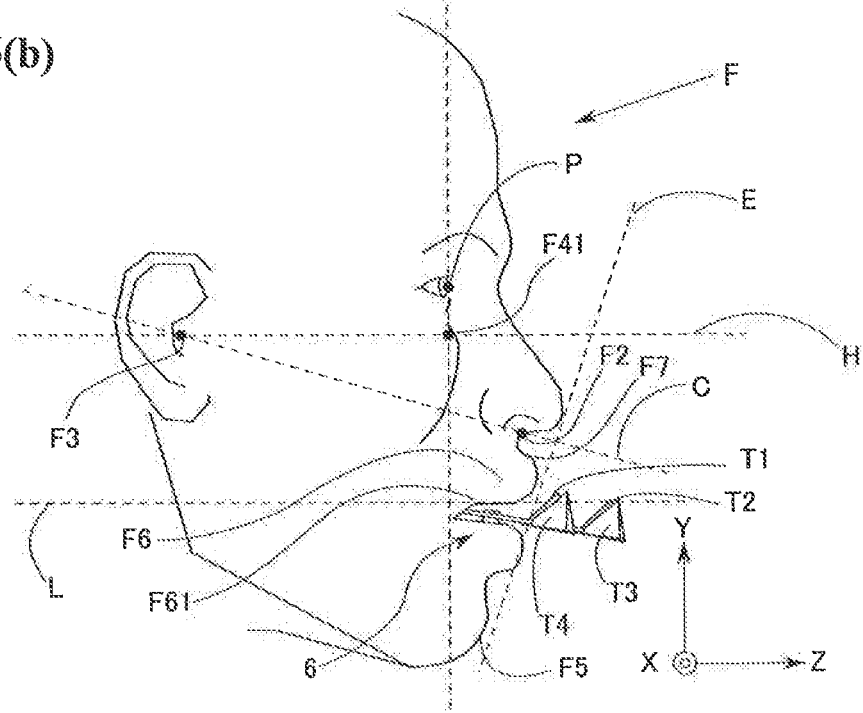

Next, as shown in FIGS. 6(a) and 6(b), with the scan targets 3 of the four jigs T1 to T4 positioned outside the mouth, the second 3D scanner 7b scans a portion of the face F that includes an area which identifies features of the face F, including any or all of the following: facial median line M; interpupillary line I; lip line L; E-line E; reference points for Camper plane; reference points for Frankfurt plane; chin F5; lips F6; mouth corners F61; and philtrum F7, and the second 3D scanner 7b also scans scan areas 30 of the scan targets 3 of the four jigs T1 to T4, thereby acquiring second three-dimensional data D2 (S3 in FIG. 2). In the present embodiment, the second 3D scanner 7b scans a portion of the face F, including all of the aforementioned features of the face F, with the lower jaw F1 being placed in rest position and the Frankfurt plane H being positioned parallel to the ground. Note that the first and second 3D scanners 7a and 7b may be the same 3D scanner. Moreover, the reference points for Camper plane refer to subnasale F2 and tragions F3, the reference points for Frankfurt plane refer to the orbital cavities' lowest points F41 and F42 and external acoustic apertures F3, the chin F5 refers to the tip of the lower jaw, and the mouth corners F61 refers to both sides of the lips F6.

Next, the analyzing device 8 analyzes the second three-dimensional data D2, thereby identifying the features of the face F and spatial positional relationships between the features of the face F and the four abutments 5a1 to 5b2 (S4 in FIG. 2).

In the present embodiment, as reference lines in X- and Y-directions for identifying positional relationships between the features of the face F and the four abutments 5a1 to 5b2, the interpupillary line I and the patient's facial median line M are used, and the intersection therebetween is set as the origin P(x0,y0) of X-Y plane. That is, in the X-Y plane, the interpupillary line I is the reference line that passes through the coordinates (x0,y0) as the X-axis, and the facial median line M is the reference line that passes through the coordinates (x0,y0) as the Y-axis.

Furthermore, in the present embodiment, used as a reference line in Z-direction is a reference line H on the Frankfurt plane, which connects the right or left orbital cavity's lowest point F41 or F42 and the upper end of the external acoustic aperture F3. That is, on the X-Y plane, the line H is a straight line serving as a reference line parallel to the Z-axis passing through the coordinates (y1,z0). Moreover, in the present embodiment, the center of the pupil in FIG. 6(b) is set as the origin (y0,z0) of the Y-Z plane.

These are merely illustrative examples, and the lip line L may be used as the reference line for the X-axis, or a line C that connects the subnasale F2 and the left or right tragion F3, both of which are reference points for Camper plane, may be used as the reference line for the Z-axis.

In an example of the method for identifying the patient's interpupillary line I, the interpupillary line I may be identified subjectively by an operator based on an image generated from the second three-dimensional data D2, or the analyzing device 8 may identify the coordinates (xe1,Ye1,ze1) and (xe2,ye2,ze2) of the centers of both pupils in the image and unambiguously identify a line that connects these coordinates as the interpupillary line I. Moreover, in the case where the 3D scanner performs scanning only with the patient's eyes closed, an image of the face F with the eyes closed is generated from the second three-dimensional data D2, and based on that image, the positions of the pupils may be estimated to identify the interpupillary line I.

In an example of the method for identifying the patient's facial median line M, the facial median line M may be identified subjectively by an operator based on an image generated from the second three-dimensional data D2, or the analyzing device 8 may unambiguously identify as the facial median line M a line that vertically and perpendicularly passes through the midpoint (xe3,Ye3,ze3) between the coordinates (xe1,Ye1,ze1) and (xe2,ye2,ze2) of the centers of the pupils.

Figure 7A:
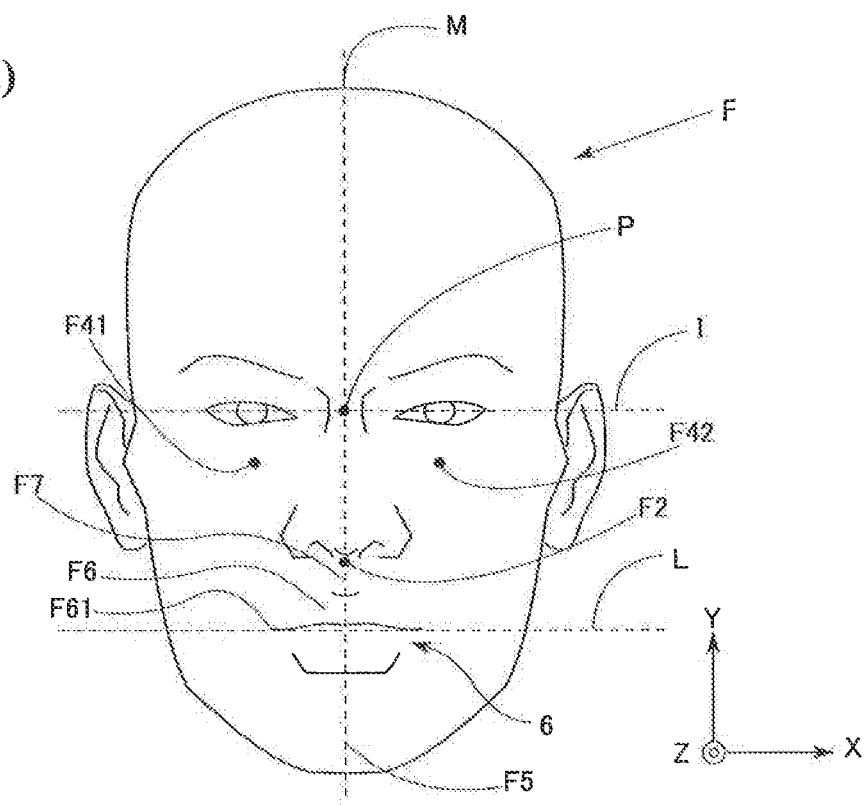
FIG. 7 provides (a) a front view and (b) a side view illustrating facial features.
Figure 7B:
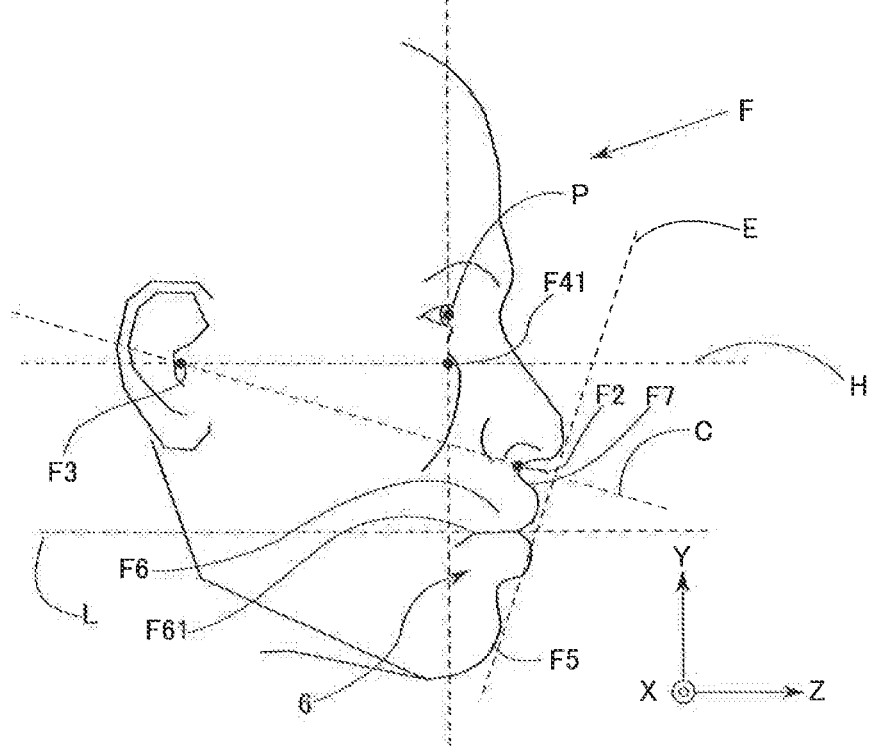

As shown in FIGS. 7(a) and 7(b), the 3D scanner may scan a portion of the face F, including an area in which the E-line E and the lip line L are visible with the jigs T being removed, and the resultant three-dimensional data may be applied to the second three-dimensional data D2 to identify the E-line E and the lip line L. In this manner, by scanning the face F with the mouth closed, the E-line E and the lip line L can be appropriately identified.

The analyzing device 8 identifies the spatial positions of the features of the face F using the X-, Y-, and Z-coordinate axes. Moreover, with reference to the X-, Y-, and Z-coordinate axes, the analyzing device 8 identifies the spatial position of each scan area 30 of the four jigs T1 to T4, then the spatial positions of each base 1 of the four jigs T1 to T4, and finally the respective spatial positions of the four abutments 5a1 to 5b2.

As a result, spatial positional relationships between the features of the patient's face F and the four abutments 5a1 to 5b2 are identified.

Next, the analyzing device 8 applies the spatial positional relationships between the features of the face F and the four abutments 5a1 to 5b2 (the second three-dimensional data D2) to the first three-dimensional data D1, thereby identifying spatial positional relationships between the features of the face F and the first three-dimensional data D1 (S5 in FIG. 2). Specifically, the spatial positions of the four abutments 5a1 to 5b2 in the second three-dimensional data D2 and the spatial positions of the four abutments 5a1 to 5b2 in the first three-dimensional data D1 are compared with each other, and the spatial positional relationships identified by the above analysis between the features of the patient's face F and the four abutments 5a1 to 5b2 (the second three-dimensional data D2) are applied to the first three-dimensional data D1, thereby identifying the spatial positions in the first three-dimensional data D1 with reference to the X-, Y-, and Z-coordinate axes.

As a result, spatial positional relationships between the features of the face F and the first three-dimensional data D1 are identified.

Next, on the basis of the first three-dimensional data D1 and the spatial positional relationships between the features of the face F and the first three-dimensional data D1, the producing device 9 produces a prosthesis 100 (S6 in FIG. 2). Specifically, based on the first three-dimensional data D1 and the spatial positional relationships between the features of the face F and the first three-dimensional data D1, three-dimensional data for the prosthesis 100, which is required by the producing device 9, is initially created. Of the three-dimensional data for the prosthesis 100, an arch angle of the prosthesis 100, tooth inclination, and tooth size are identified in advance based on, for example, information about remaining teeth in the upper jaw F8. Moreover, positions and inclinations of four holes (referred to below as "access holes"), which are to be provided in the prosthesis 100 in order to connect the prosthesis 100 to the four abutments 5a1 to 5b2, are identified based on the first three-dimensional data D1 and the spatial positional relationships between the features of the face F and the first three-dimensional data D1. Specifically, based on the first three-dimensional data D1, spatial positional relationships between the access holes are initially identified, and then, based on the spatial positional relationships between the features of the face F and the first three-dimensional data D1, it is verified whether the positions and inclinations of the access holes are appropriate.

The verification may be performed based on a simulation image generated by the analyzing device 8. In a method for generating the simulation image, the spatial positions of the access holes in the three-dimensional data for the prosthesis 100 to be produced, and the spatial positions of the four abutments 5a1 to 5b2 in the first three-dimensional data D1 are initially compared with each other, and spatial positional relationships between the features of the patient's face F and the four abutments 5a1 to 5b2 are applied to the three-dimensional data for the prosthesis 100. As a result, the spatial positions in the three-dimensional data for the prosthesis 100 are identified with reference to the X-, Y-, and Z-coordinate axes.

Figure 8:
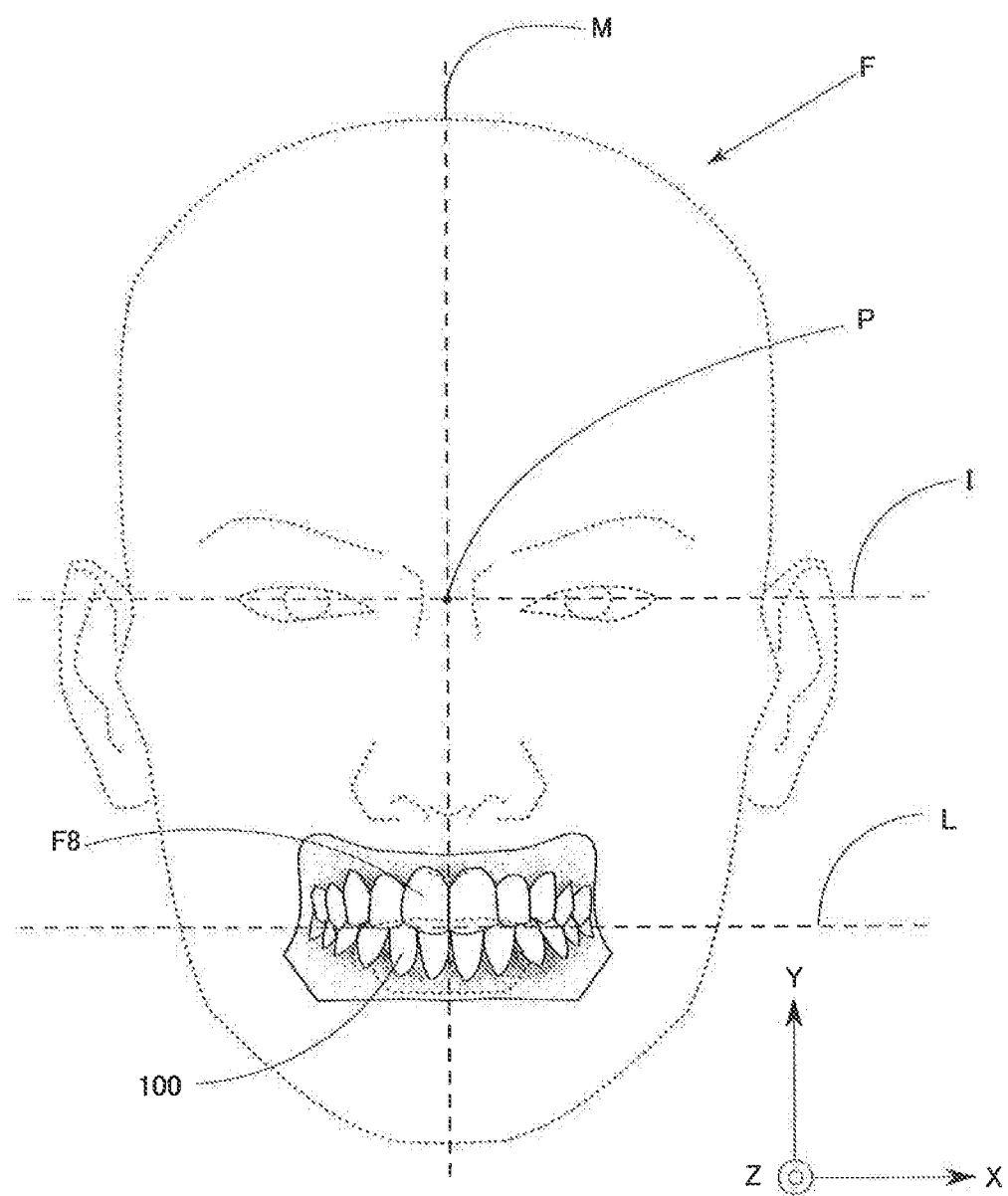
FIG. 8 is a diagram illustrating a simulation image obtained by combining a facial image and an intraoral image.

Next, the analyzing device generates a simulation image as shown in FIG. 8. Specifically, based on the identified spatial positions in the three-dimensional data for the prosthesis 100, the analyzing device 8 combines an image of the face F generated based on the second three-dimensional data D2, an image of the prosthesis 100 generated based on the three-dimensional data for the prosthesis 100, and an image of the upper jaw (teeth) F8 generated based on the first three-dimensional data D1, thereby generating a simulation image. With the simulation image, the producer of the prosthesis 100 and the patient can confirm spatial positional relationships between the features of the face F and the prosthesis 100 before the production of the prosthesis 100.

Specifically, the verification is performed based on, for example, whether the facial median line M matches the center of the prosthesis 100 to be produced, whether the interpupillary line I is parallel to the occlusal plane of the prosthesis 100 to be produced, and whether the position of the prosthesis 100 to be produced in the Z-axis direction with respect to the E-line E is appropriate.

Next, on the basis of the verification result, the three-dimensional data for the prosthesis 100 is corrected in terms of the positions and inclinations of the access holes, thereby creating final three-dimensional data for the prosthesis 100.

Next, the prosthesis 100 is produced by controlling the producing device 9 in accordance with the created three-dimensional data for the prosthesis 100. The producing device 9 is, for example, a milling machine or a three-dimensional printer.

The prosthesis 100 as above, which is produced on the basis of a combination of intraoral information and information about the features of the face F, can satisfy both functional and aesthetic requirements. Moreover, since functionality and aesthetics of the prosthesis 100 can be confirmed before the production, it is possible to reduce corrections to the prosthesis 100 after the production. Thus, it is rendered possible to achieve the effects of reducing financial burden on the patient for implant treatment and shortening the term of treatment.

Second Embodiment

Next, a method in which an intraoral image and a facial image are combined using scanning jigs of the present invention will be described taking as an example dental implant treatment for a missing tooth.

<Scanning Jig>

Figure 9A:
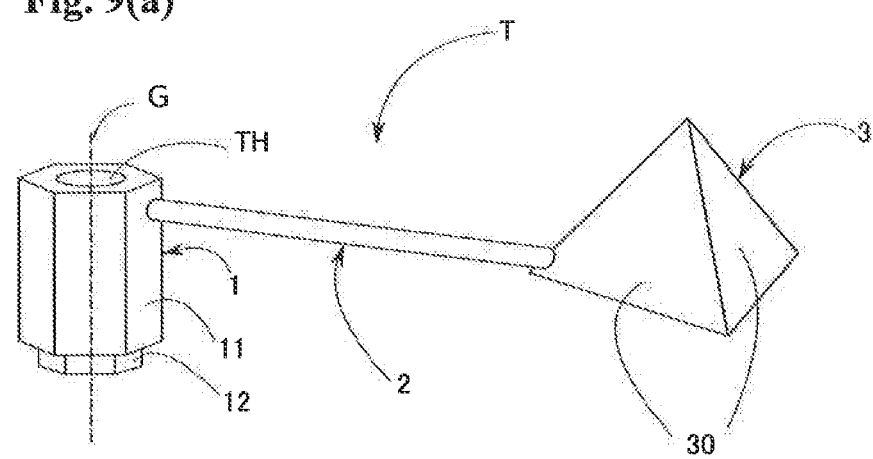
FIG. 9 provides (a) an oblique view illustrating a scanning jig of the present invention, along with an implant body and an abutment different from those in FIGS. 1 and 2, and (b) a vertical cross-sectional view taken along the center axis of a base of the scanning jig.
Figure 9A:
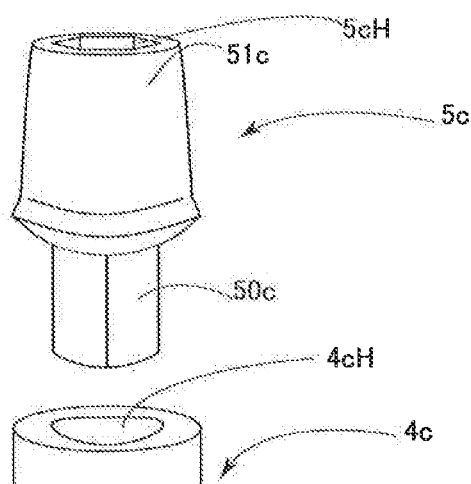

FIG. 9(a) is an oblique view illustrating a scanning jig T (simply referred to below as a "jig T") according to a second embodiment of the present invention, along with an abutment 5c to be connected to the jig T, and an implant body 4c to be connected to the abutment 5c. The jig T in the present embodiment differs from the jig T1 in FIG. 1(a) in that the base 1 has a different shape, but all other elements are common. Accordingly, the common elements are denoted by the same numbers and will not be elaborated upon.

The implant body 4c and the abutment 5c are members mainly for use in implant treatment in which one tooth is supported by one implant body. The implant body 4c has an internally threaded triangular hole 4cH provided at an upper end.

The abutment 5c includes a lower connecting portion 50c, an abutment body 51c, and a hexagonal threaded hole 5cH. The threaded hole 5cH is an internally threaded multi-stage hole. The lower connecting portion 50c has a triangular prism shape. The lower connecting portion 50c is configured to be inserted into and engaged with the triangular hole 4cH by a screw (not shown) inserted into the threaded hole 5cH.

The jig T includes a base 1, a connecting portion 2, and a scan target 3.

The base 1 has a hexagonal-prism connecting portion 12, a base body 11 stepped and widened from an upper end of the hexagonal-prism connecting portion 12, and a threaded hole T2H provided at the center of an upper end of the base body 11.

The hexagonal-prism connecting portion 12 is configured to be inserted into the threaded hole 5cH so as not to be rotatable.

The base body 11 is formed in the shape of a hexagonal prism extending in a direction along a centrally vertical axis G of the base 1, but this is merely an illustrative example and is not limiting.

Figure 9B:
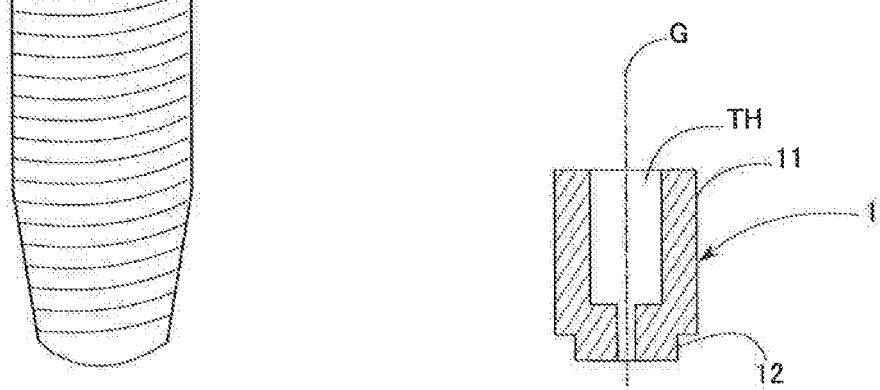

The stepped through hole TH is provided along the centrally vertical axis G of the base 1, as shown in FIG. 9(b). The stepped through hole TH is configured to receive a screw (not shown) by which the base 1 is removably engaged with the abutment body 51c.

The connecting portion 2 is connected to an upper end portion of the base body 11 so as to be a bridge between the base 1 and the scan target 3.

The jig T thus configured has a scan area 30 to be scanned by a 3D scanner, with the result that an analysis is conducted in the same manner as in the first embodiment, whereby the spatial position of the abutment 5c connected to the base 1 is identified.

<Method for Combining the Intraoral Image and the Facial Image>

Next, a method for combining an intraoral image and a facial image will be described with reference to FIGS. 10 to 12.

Figure 11A:
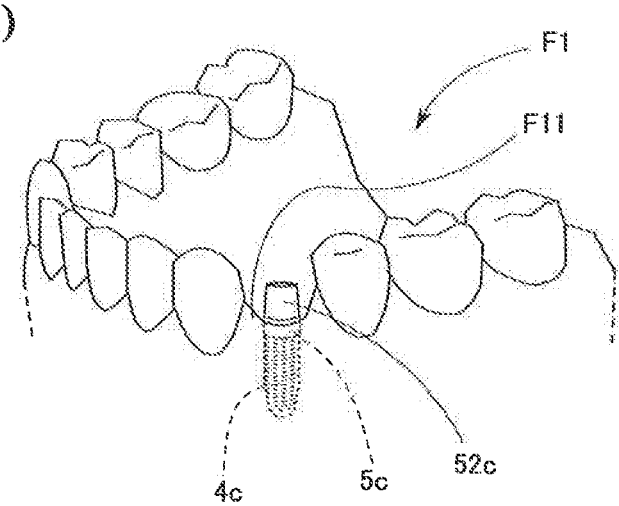
FIG. 11 provides (a) an oblique view illustrating the implant body and the abutment in FIG. 9 placed in a lower jaw, and (b) an oblique view illustrating the scanning jig in FIG. 9 connected to the abutment.

First, the implant body 4c is inserted into the lower jaw F1 in the same manner as in the first embodiment, as shown in FIG. 11(a). The abutment 5c is connected to the implant body 4c.

Figure 10:
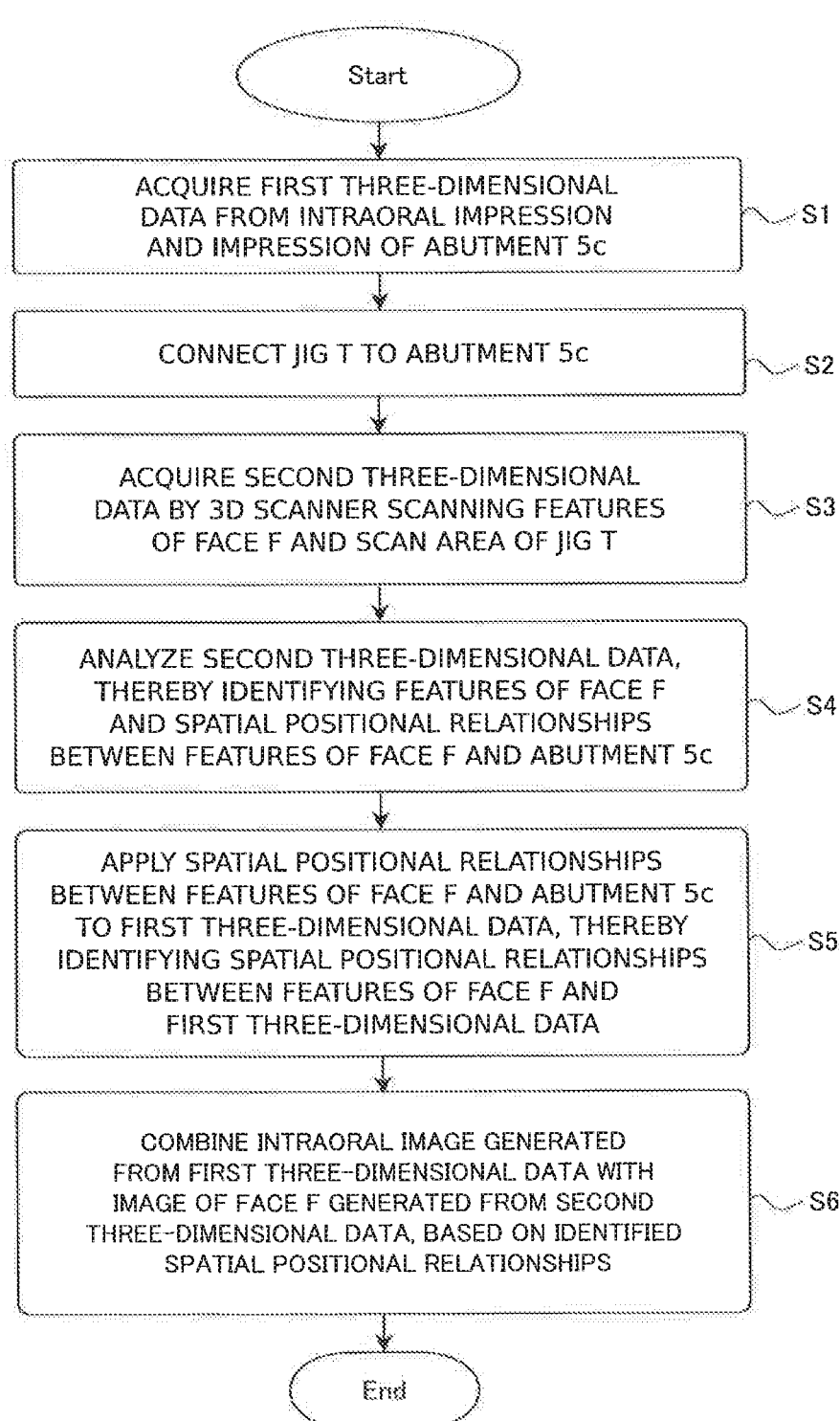
FIG. 10 is a flowchart of a method for identifying spatial positional relationships between facial features and first three-dimensional data using the scanning jig in FIG. 9.

Next, first three-dimensional data D1 is acquired from an intraoral impression and an impression of the placed abutment 5c in the same manner as in the first embodiment (S1 in FIG. 10).

Figure 11B:
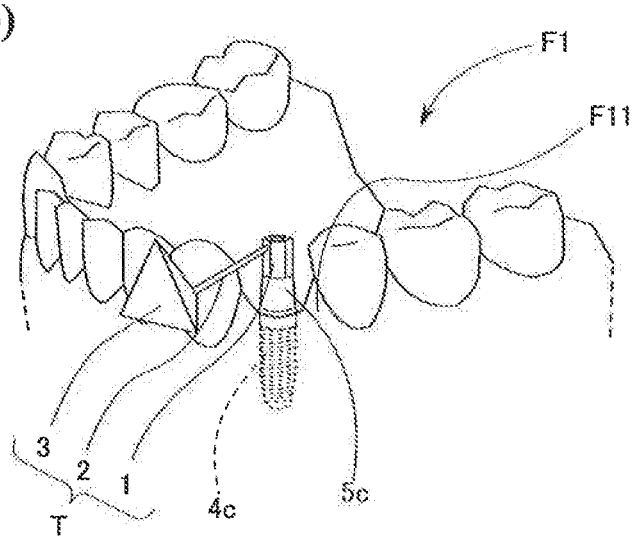

Next, the jig T is connected to and threadedly engaged with the abutment 5c (S2 in FIG. 10), such that the scan target 3 is positioned in front with as little contact as possible with teeth in the mouth, as shown in FIG. 11(b).

Figure 12A:
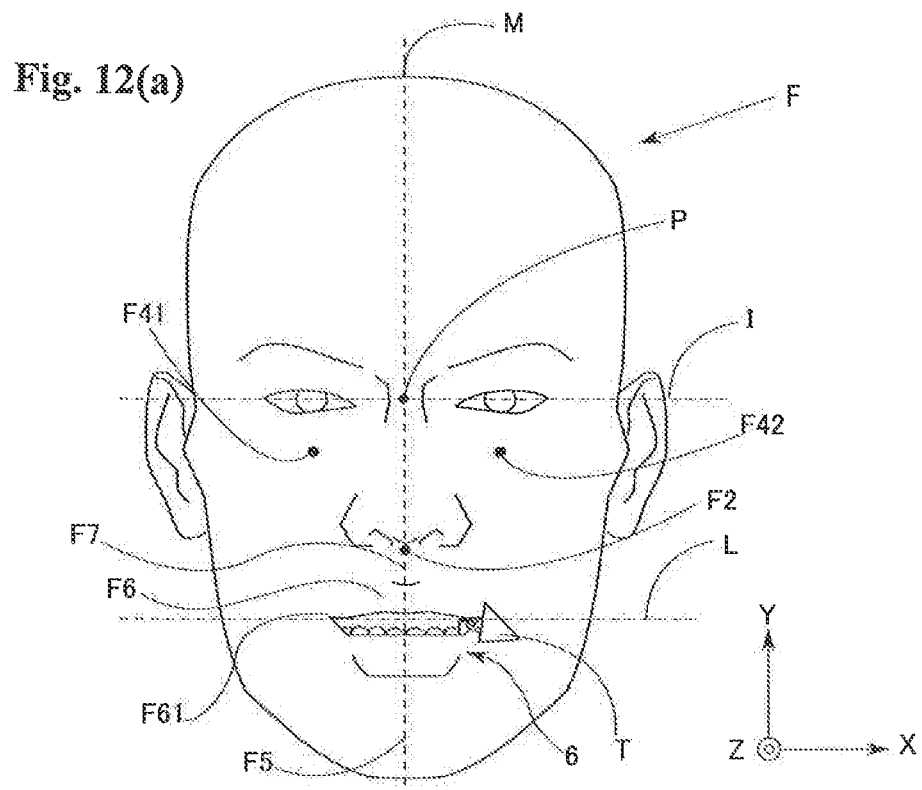
FIG. 12 provides (a) a front view and (b) a side view illustrating a face and the scanning jig in FIG. 9 connected to the abutment in a mouth.
Figure 12B:
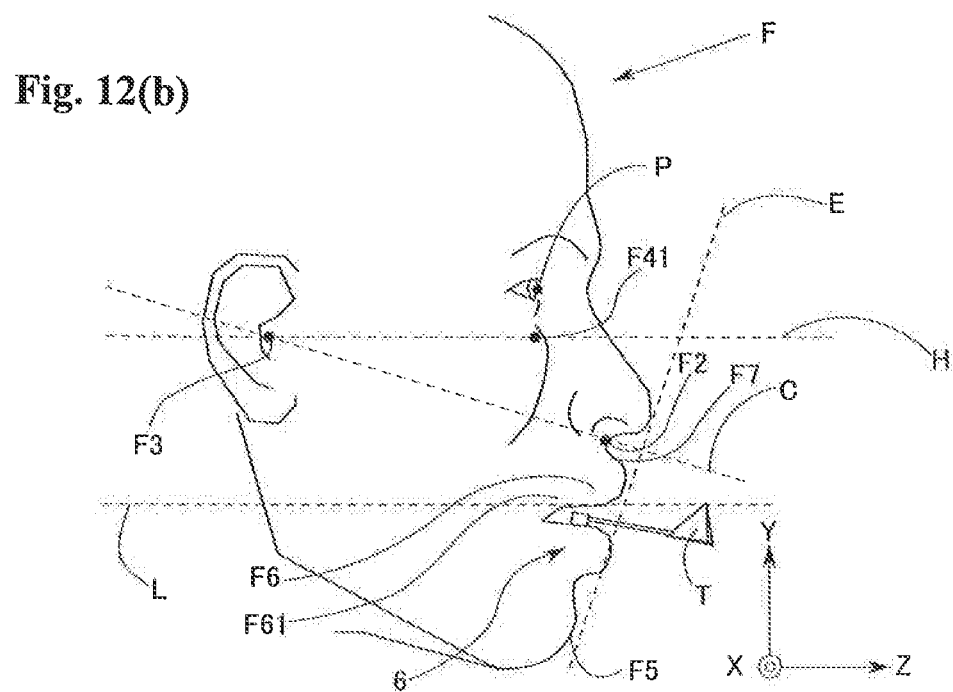

Next, with the scan target 3 positioned outside the mouth, as shown in FIGS. 12(a) and 12(b), a portion of the face F and the scan area 30 of the jig T are scanned by a 3D scanner in the same manner as in the first embodiment, thereby acquiring second three-dimensional data D2 (S3 in FIG. 10). The portion of the face F includes an area which identifies features of the face F, including any or all of the following: facial median line M; interpupillary line I; lip line L; E-line E; reference points for Camper plane (i.e., subnasale F2 and tragions F3); reference points for Frankfurt plane (i.e., external acoustic apertures F3, and orbital cavities' lowest points F41 and F42); chin F5; lips F6; mouth corners F61; and philtrum F7.

Next, an analyzing device analyzes the second three-dimensional data D2, thereby identifying features of the face F and spatial positional relationships between the features of the face F and the abutment 5c (S4 in FIG. 10). More specifically, in the same manner as in the first embodiment, features of the face F, which are used for reference lines in the X-, Y-, and Z-directions, are identified based on three-dimensional data for the face F included in the second three-dimensional data D2, thereby identifying the X-, Y-, and Z-coordinate axes and the origin P based on the reference lines that are based on the identified features of the face F.

Next, in the same manner as in the first embodiment, the spatial position of the base 1 of the jig T are identified with reference to the X-, Y-, and Z-coordinate axes, and then the spatial position of the abutment 5c is identified. Moreover, in the same manner as in the first embodiment, the spatial position of each feature of the face F is also identified based on the same coordinate axes. As a result, the spatial positional relationships between the features of the patient's face F and the abutment 5c is identified.

Next, in the same manner as in the first embodiment, the spatial positional relationships between the features of the face F and the abutment 5c (the second three-dimensional data D2) are applied to the first three-dimensional data D1, thereby identifying spatial positional relationships between the features of the face F and the first three-dimensional data D1 (S5 in FIG. 10).

Next, on the basis of the identified spatial positional relationships between the features of the face F and the first three-dimensional data D1, an image is obtained by combining an intraoral image generated from the first three-dimensional data D1 and an image of a portion of the face F generated from the second three-dimensional data D2 (S6 in FIG. 10). Thus, for example, the spatial position of an externally threaded portion in three-dimensional data for a prosthesis to be produced is compared with the spatial position of the threaded hole 5cH of the abutment 5c in the first three-dimensional data D1, thereby identifying spatial positional relationships between the first three-dimensional data D1 and the three-dimensional data for the prosthesis, and the resultant composite image is further combined with an image generated from the three-dimensional data for the prosthesis, thereby generating a simulation image.

Accordingly, on the basis of the simulation image, the producer of the prosthesis and the patient can confirm spatial positional relationships between the face F and the prosthesis to be produced, before the production of the prosthesis.

While preferred embodiments of the scanning jig according to the present invention have been described, the present invention is not limited to the embodiments.

The base 1 of the jig T may be connected to the implant body. In such a case, the scan target 3 is scanned by the 3D scanner, thereby acquiring three-dimensional data, with the result that the spatial position of the implant body connected to the jig T1 or T2 is identified.

The implant body and the abutment that are connected to the base 1 are not limited to specific forms, and, for example, the implant body and the abutment may be integrated as a one-piece implant body.

The portion at which the base 1 is connected to one end of the connecting portion 2 is not limited to the side surface of the base 1, and may be the upper end surface of the base 1. In such a case, the connecting portion 2 may have a flexure in a middle portion and be bent at the flexure such that the other end of the connecting portion 2 is positioned outside the mouth.

The connecting portion 2 may be connected to the base 1 and the scan target 3 so as to be removable from either the base 1 or the scan target 3, or both.

Figure 13A:
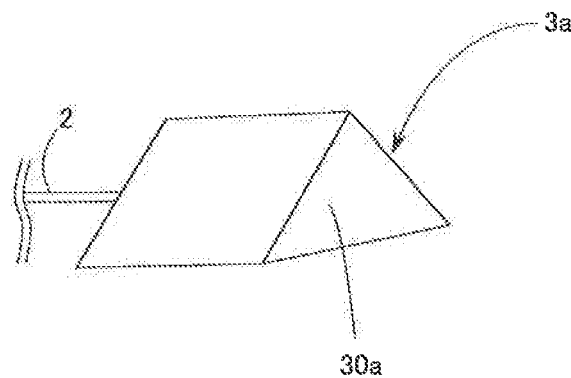
FIG. 13 provides oblique views illustrating variants of the scanning jig according to the present invention.
Figure 13B:
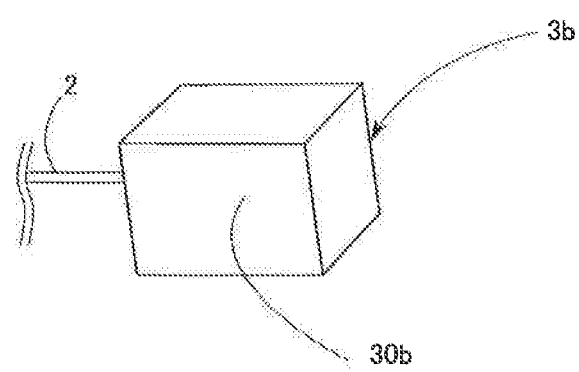
Figure 13C:
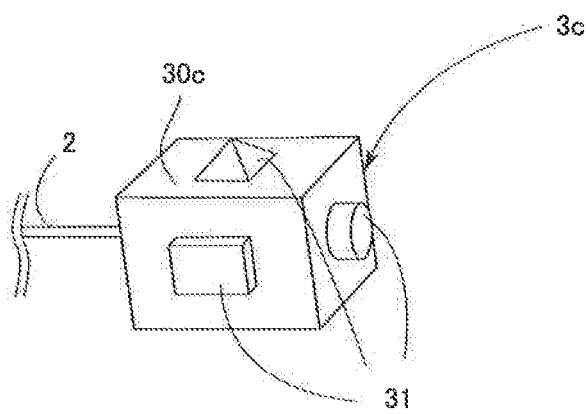

The shape of the scan target 3 is not specifically limited, and may be, for example, a triangular prism or a rectangular solid, as represented by scan targets 3a, 3b, and 3c shown in FIGS. 13(a), 13(b), and 13(c). Moreover, the scan area 30 may be a portion of the surface of the scan target 3a, 3b, or 3c, so long as the spatial position of the scan target 3a, 3b, or 3c can be identified by the 3D scanner scanning the scan area 30. Moreover, the scan area may have markers 31 to be used as indicators for 3D scanning, as shown in FIG. 13(c). The indication marker may be either a two-dimensional marker or a three-dimensional marker as exemplified by the marker 31.

The scan area 30 preferably has a flat surface so as to be optimally scanned by the 3D scanner. Moreover, the scan area 30 preferably has such flat surfaces in more than one direction so as to be scanned by the 3D scanner from multiple directions.

To prevent deformation of the jigs T1 and T2 due to own weight and surrounding environment, the jigs T1 and T2 preferably are lightweight and have some mechanical strength. Accordingly, the jigs T1 and T2 may be made of, for example, polyetheetherketone (PEEK), whose relative density is low and which has superior heat resistance and mechanical strength.

DESCRIPTION OF THE REFERENCE CHARACTERS

T scanning jig
TH stepped through hole
1 base
10 truncated conical connecting portion
11 base body
2 connecting portion 3, 3a, 3b, 3c scan target
30, 30a, 30b, 30c scan area
31 marker
4a, 4b, 4c implant body
4aH round hole
4bH hexagonal hole
4cH triangular hole
5a, 5b, 5c abutment
50a, 50b, 50c lower connecting portion
51a, 51c abutment body
52a, 52b upper connecting portion
53 angle-corrected portion
7a first 3D scanner
7b second 3D scanner
8 analyzing device
9 producing device
100 prosthesis
B1 intraoral model
B2 scan body
C reference line for Camper plane
D1 first three-dimensional data
D2 second three-dimensional data
E E-line
F face
F1 lower jaw
F11 gingiva
F2 subnasale
F3 external acoustic aperture or tragion
F41, F42 orbital cavities' lowest point
F5 chin
F6 lip
F61 mouth corner
F7 philtrum
F8 upper jaw (teeth)
H reference line for Frankfurt plane
I interpupillary line
L lip line
M facial median line
P origin

The invention claimed is:

1. A scanning jig adapted for identifying a spatial positional relationship between a portion of a patient's facial features and an abutment, the abutment being connected to an implant body placed in a patient's jaw and having (i) an upper connecting portion comprising a top surface and (ii) a threaded hole extending downward vertically from the top surface for a prosthesis to be secured, the upper connecting portion being a female connection portion or a male connection portion, the scanning jig comprising:
 a base comprising a base body being an elongated cylindrical or polygonal prismatic tube having an upper end region and a lower end region and a base connecting portion below the lower end region of the base body, the base connecting portion being a male connection portion when the upper connecting portion of the abutment is a female connection portion or being a female connection portion when the upper connecting portion of the abutment is a male connection portion, the base connecting portion being configured to engage the upper connecting portion of the abutment and comprising a stepped through hole extending downward vertically through the base body and the base connecting portion, the stepped through hole adapted for removable connection of the base to the threaded hole in the abutment by a screw, the stepped through hole being the sole stepped through hole through the base;
 a scan target having a scan area adapted for being scanned by a 3D scanner capable of scanning a portion of the patient's facial features and the scan area; and
 a connecting portion connecting the base and the scan target, the connecting portion comprising an elongated bar having a first end attached to the upper end region of the base body and a second end attached to the scan target and having a predetermined length such that, when the base is connected to the abutment, the scan target is positioned outside the patient's mouth,
 wherein the stepped through hole is configured to guide the screw that is screwed into the abutment and is positioned on the same axis as the threaded hole of the abutment when the base connecting portion is secured to the abutment by the screw,
 wherein the spatial positional relationship includes the positional relationship between a portion of the patient's facial features and the orientation of the threaded hole in the abutment.

2. The scanning jig according to claim 1, wherein the base has a predetermined height that allows the base to be placed in the patient's mouth.

3. The scanning jig according to claim 1, wherein the connecting portion is removably connected to either the base or the scan target, or both.

4. The scanning jig according to claim 1, wherein the scan area has a flat surface.

5. The scanning jig according to claim 1, wherein the scan area has either a two-dimensional marker or a three-dimensional marker, or both.

6. The scanning jig according to claim 1, wherein the connecting portion extends substantially perpendicularly from the upper end region of the base body.

7. The scanning jig according to claim 1, the base connecting portion being the male connection portion when the upper connection portion of the abutment is a female connection portion, and the base connecting portion has a concave, truncated conical portion in its lower part configured to engage the upper connecting portion of the abutment and is thereby placed over the abutment and connected to the abutment.

8. The scanning jig according to claim 1, the base connecting portion being the female connection portion when the upper connection portion of the abutment is a male connection portion, and the base connecting portion has a convex, polygonal prismatic section in its lower part configured to engage a recess in the upper connecting portion of the abutment and is thereby fitted into the abutment and connected to the abutment.

9. The scanning jig according to claim 1, wherein the scan target is polygonal in shape.

10. A method for identifying spatial positional relationships between a portion of the face and an abutment connected to an implant body placed in a patient's jaw, the abutment having a threaded hole extending downward vertically from its top surface for a prosthesis to be secured, comprising:
 connecting the base of the scanning jig of claim 1 to the abutment by a screw with the stepped through hole in the base and the threaded hole positioned on the same axis;
 acquiring three-dimensional data by the 3D scanner scanning at least a portion of the face besides the jaw and the scan area, with the scan target positioned outside the patient's mouth; and analyzing the three-dimensional data, thereby identifying spatial positional relationships between the portion of the face and the implant body.

11. A method for identifying spatial positional relationships between features of the face and an abutment connected to an implant body placed in a patient's jaw, the abutment having a threaded hole extending downwardly vertically from its top surface for a prosthesis to be secured, comprising:
connecting the base of the scanning jig of claim 1 to the abutment by a screw with the stepped through hole in the base and the threaded hole of the abutment positioned on the same axis;
acquiring three-dimensional data by the 3D scanner scanning the scan area and a portion of the face besides the jaw that includes an area identifying the features of the face, with the scan target positioned outside the patient's mouth, the features of the face including any or all of the following: facial median line; interpupillary line; lip line; E-line; reference points for Camper plane; reference points for Frankfurt plane; chin; lips; mouth corners; and philtrum; and
analyzing the three-dimensional data, thereby identifying the features of the face and the spatial positional relationships between the abutment and the features of the face.

12. A method for combining an image of an impression of the mouth and an image of the face, comprising:
connecting the base of the scanning jig of claim 1 to an abutment by a screw, the abutment being connected to an implant body placed in a patient's jaw and having a threaded hole extending downward vertically from its top surface, with the stepped through hole in the base and the threaded hole of the abutment positioned on the same axis;
acquiring first three-dimensional data for the patient's mouth and the abutment from the impression of the patient's mouth;
acquiring second three-dimensional data by the 3D scanner scanning at least a portion of the face besides the jaw and the scan area, with the scan target positioned outside the mouth;
analyzing the second three-dimensional data, thereby identifying spatial positional relationships between the portion of the face and the abutment;
comparing a spatial position of the abutment in the second three-dimensional data and a spatial position of the implant in the first three-dimensional data and applying the spatial positional relationships between the portion of the face and the implant to the first three-dimensional data, thereby identifying spatial positional relationships between the portion of the face and the first three-dimensional data; and
combining an image of the mouth generated from the first three-dimensional data with an image of the portion of the face generated from the second three-dimensional data, based on the spatial positional relationships between the portion of the face and the first three-dimensional data.

13. A method for producing a dental prosthesis, comprising: connecting the base of the scanning jig of claim 1 to an abutment by a screw, the abutment being connected to an implant body placed in the patient's jaw and having a threaded hole extending downward vertically from its top surface with the stepped through hole in the base and the threaded hole of the abutment positioned on the same axis;
acquiring first three-dimensional data for the patient's mouth and the abutment from an impression of the mouth and an impression of the abutment;
acquiring second three-dimensional data by the 3D scanner scanning at least a portion of the face besides the jaw and the scan area, with the scan target positioned outside the mouth;
analyzing the second three-dimensional data, thereby identifying spatial positional relationships between the portion of the face and the abutment;
comparing a spatial position of the abutment in the second three-dimensional data and a spatial position of the abutment in the first three-dimensional data and applying the spatial positional relationships between the portion of the face and the abutment to the first three-dimensional data, thereby identifying spatial positional relationships between the portion of the face and the first three-dimensional data; and
producing the prosthesis based on the first three-dimensional data and the spatial positional relationships between the portion of the face and the first three-dimensional data.

14. A method for producing an implant bridge prosthesis, comprising:
providing a plurality of scanning jigs of claim 1; connecting the bases of the plurality of scanning jigs respectively to a plurality of abutments by screws, each abutment having a threaded hole extending downward vertically from its top surface and being connected to an implant body placed in a patient's jaw, the plurality of the abutments connectable to one implant bridge;
acquiring first three-dimensional data for the patient's mouth and the abutments from an impression of the mouth and an impression of the abutments;
acquiring second three-dimensional data by the 3D scanner scanning a portion of the face besides the jaw and the scan areas of a plurality of the scan targets, with the scan targets positioned outside the mouth, the portion of the face including an area identifying features of the face, including any or all of the following: facial median line; interpupillary line; lip line; E-line; reference points for Camper plane; reference points for Frankfurt plane; chin; lips; mouth corners; and philtrum;
analyzing the second three-dimensional data, thereby identifying the features of the face and spatial positional relationships between the features of the face and the abutments;
comparing spatial positions of the abutments in the second three-dimensional data and spatial positions of the abutments in the first three-dimensional data and applying the spatial positional relationships between the features of the face and the abutments to the first three-dimensional data, thereby identifying spatial positional relationships between the features of the face and the first three-dimensional data; and
producing the prosthesis based on the first three-dimensional data and the spatial positional relationships between the features of the face and the first three-dimensional data,
wherein when the bases are connected respectively to the plurality of the abutments by the screws, the female thread and the stepped through hole are positioned respectively on the same axis.

15. A system for producing an implant bridge prosthesis, comprising:

providing a plurality of scanning jigs of claim 1; the plurality of scanning jigs being adapted to be connected respectively by screws to a plurality of abutments, the plurality of the abutments connectable to one implant bridge, each abutment having a threaded hole extending downward vertically from its top surface and being connected to an implant body placed in a patient's jaw;

a first 3D scanner acquiring first three-dimensional data for the patient's mouth and the abutments from an impression of the mouth and an impression of the abutments;

a second 3D scanner acquiring second three-dimensional data by scanning a portion of the patient's face besides the jaw and scan areas of the plurality of scan targets of the plurality of scanning jigs, with the scan targets positioned outside the mouth, the portion of the face including an area identifying features of the face, including any or all of the following: facial median line; interpupillary line; lip line; E-line; reference points for Camper plane; reference points for Frankfurt plane; chin; lips; mouth corners; and philtrum;

an analyzing device analyzing the second three-dimensional data, identifying the features of the face and spatial positional relationships between the features of the face and the abutments, comparing spatial positions of the abutments in the second three-dimensional data and spatial positions of the abutments in the first three-dimensional data, and applying the spatial positional relationships between the features of the face and the abutments to the first three-dimensional data, thereby identifying spatial positional relationships between the features of the face and the first three-dimensional data; and a producing device producing the prosthesis under control in accordance with three-dimensional data for the prosthesis, the three-dimensional data being created based on the first three-dimensional data and the spatial positional relationships between the features of the face and the first three-dimensional data, wherein when the bases are connected respectively to the plurality of the abutments by the screws, the threaded hole of the abutment and the stepped through hole are positioned respectively on the same axis.

* * * * *